United States Patent
Vaughn

(10) Patent No.: US 9,572,616 B2
(45) Date of Patent: Feb. 21, 2017

(54) CONTINUOUS RATCHET MEDICAL INSTRUMENT DRIVE

(71) Applicant: Tyrone Vaughn, Kenosha, WI (US)

(72) Inventor: Tyrone Vaughn, Kenosha, WI (US)

(73) Assignee: Bradshaw Medical, Inc., Kenosha, WI (US)

( * ) Notice: Subject to any disclaimer, the term of this patent is extended or adjusted under 35 U.S.C. 154(b) by 371 days.

(21) Appl. No.: 14/472,498

(22) Filed: Aug. 29, 2014

(65) Prior Publication Data

US 2015/0059499 A1    Mar. 5, 2015

Related U.S. Application Data

(60) Provisional application No. 61/873,475, filed on Sep. 4, 2013.

(51) Int. Cl.
| | | |
|---|---|---|
| *F16H 19/02* | (2006.01) | |
| *A61B 17/00* | (2006.01) | |
| *A61B 17/88* | (2006.01) | |
| *B25B 15/04* | (2006.01) | |
| *B25B 17/02* | (2006.01) | |

(52) U.S. Cl.
CPC .......... *A61B 17/8875* (2013.01); *B25B 15/04* (2013.01); *B25B 17/02* (2013.01); *Y10T 74/18416* (2015.01)

(58) Field of Classification Search
CPC ..... A61B 17/8875; A61B 17/00; B25B 15/04; B25B 17/02
See application file for complete search history.

(56) References Cited

U.S. PATENT DOCUMENTS

| | | | | |
|---|---|---|---|---|
| 3,124,010 A | * | 3/1964 | Eady | B25B 13/466 74/130 |
| 4,427,100 A | * | 1/1984 | Rude | B25B 13/462 192/41 S |
| 5,176,038 A | | 1/1993 | Inokuchi et al. | |
| 5,259,259 A | | 11/1993 | Inokuchi et al. | |
| 5,931,062 A | * | 8/1999 | Marcovici | B25B 13/467 81/177.2 |
| 8,707,831 B2 | * | 4/2014 | Palmer | B25B 13/463 74/810.1 |
| 9,086,103 B2 | * | 7/2015 | Takada | F16D 41/066 |
| 9,114,510 B2 | * | 8/2015 | Lee | B25B 13/463 |
| 9,333,630 B2 | * | 5/2016 | Palmer | B25B 15/04 |
| 9,334,926 B2 | * | 5/2016 | Takahashi | F02D 15/02 |
| 2010/0043603 A1 | * | 2/2010 | McRoberts | B25B 13/465 81/57.11 |
| 2010/0286791 A1 | * | 11/2010 | Goldsmith | A61B 17/12022 623/23.7 |

(Continued)

FOREIGN PATENT DOCUMENTS

EP    2586570 A1    5/2013

*Primary Examiner* — David M Fenstermacher
(74) *Attorney, Agent, or Firm* — Absolute Technology Law Group, LLC

(57) ABSTRACT

The present invention is a continuous medical instrument adapter that safely provides a 180-degree torque force during a surgical procedure while accommodating the range of motion of the surgeon's hand during the surgical procedure. The drive mechanism of said adapter is capable of non-lubricated function, enabling it to be used in a medical environment and to be sterilized without loss of function.

20 Claims, 8 Drawing Sheets

(56) References Cited

U.S. PATENT DOCUMENTS

| | | | |
|---|---|---|---|
| 2012/0103142 A1* | 5/2012 | Sroka | B25B 13/48 81/57.11 |
| 2014/0039343 A1* | 2/2014 | Mescher | A61B 10/0275 600/563 |
| 2014/0083259 A1* | 3/2014 | Anderson | B25B 13/463 81/63.1 |
| 2015/0059499 A1* | 3/2015 | Vaughn | A61B 17/8875 74/70 |

* cited by examiner

CONTINUOUS RATCHET MEDICAL INSTRUMENT DRIVE

CROSS-REFERENCE TO RELATED APPLICATIONS

This application is a non-provisional application of and claims priority to U.S. Patent Application 61/873,475, filed on Sep. 4, 2013, which is hereby incorporated by reference in its entirety.

FIELD OF INVENTION

The present invention relates to the field of medical instruments and more specifically a medical instrument system adapter that safely provides a 180-degree torque force during a surgical procedure while accommodating the range of motion of the surgeon's hand during the surgical procedure.

BACKGROUND

Continuous ratchet drive assemblies are known in the art and used for many applications in tools and machinery. A continuous ratchet drive assembly is characterized by the capability of the gear assembly to receive two input torque forces applied from two different directions and to translate the bi-directional input forces to an output force in a single direction.

There are many situations in which it is desirable for a dual input torque to produce a single output torque because either a human hand or a gear cannot accommodate 180-degree rotation. Continuous ratchet motion is intended to prevent the loss of half the input torque motion.

During a surgical procedure, it is desirable to accommodate the range of motion of a surgeon's hand and to use force effectively, by applying it to the instrument in order to avoid fatigue. However, it has not been possible to apply mechanical principals used for tools and other continuous ratchet drive assemblies to medical instruments.

This is primarily because the instruments known in the prior art rely on entraining mechanisms which engage and slide mechanical components either over or past each other. Entraining mechanisms involve contact between two or more metal components and require lubrication. However, surgical instruments cannot use lubricants. Tools known in the prior art rely upon parts that generally require the use of lubricants or non-medical grade coatings. Additionally, the movement of these assemblies is not precise or stable enough to withstand medical procedures and subsequent sterilization.

Without lubrication, medical instruments are prone to galling. Galling is a form of wear characterized by localized material transfer, removal, or formation of protrusions when two solid surfaces slide against each other.

It is a problem known in the art that medical instruments must be non-galling and capable of functioning without lubricants.

It is also a problem known in the art that all components and assemblies within a medical instrument must be safe, stable, and capable of high precision and smooth movement.

For example, U.S. Pat. No. 5,931,062 (Marcovici '062) discloses a continuous ratchet drive gear assembly having a reversing mechanism coupling two driving elements. This coupling forces the two ratchet gears together forcing them to always rotate in opposite directions so that one driving element entrains the shaft and the other driving element overruns the shaft. This causes the shaft to always turn in only one direction, regardless of the direction of rotation of the driving elements. The apparatus taught in Marcovici '062 cannot be used in medical instruments because it requires entraining.

The entraining mechanism taught by Marcovici '062 involves substantial sliding contact between two metal elements requiring use of lubrication.

For example, U.S. Pat. No. 5,176,038 (Inokuchi I '038) and U.S. Pat. No. 5,259,259 (Inokuchi II '259) disclose a mechanism to convert the linearly reciprocating motion of a radial handle into a unidirectional rotation of an output shaft through a racks and pinion combination utilizing toothed one-way clutches capable of selective deactivation to reverse output shaft rotation. During operation, the pinions slide in contact with a stationary plate, requiring application of lubricant between the metal surfaces that will be in contact. Similarly, the drive gears situated on shafts have metal surfaces that slide in contact with the bottom surface of the sun gear during rotation, which likewise requires application of a lubricant between the metal surfaces of the drive gears and the sun gear to prevent galling and corrosion.

In another example, European patent 2,586,570 A1 (Wang '570) discloses a manual tool having a bidirectional mechanical converting means. In one embodiment, a bidirectional mechanical conversion scheme with a reversing means comprising a reversing element sleeved on the main shaft with openings through which pawls can engage with the toothed inner surface to form a one-way clutch and an elastic element between each pair of pawls to keep the pawls diverging against the toothed inner surface. However, the use of an elastic element cannot be autoclaved and thus precludes use of the reversing mechanism for medical use. Further, an elastic element will not provide the required smooth rotational motion required for use in surgical procedures.

It is desirable to adapt this concept to a medical tool, but there are many engineering issues to overcome, including the use of lubricants and the need to prevent galling.

TERMS OF ART

Figure 1:
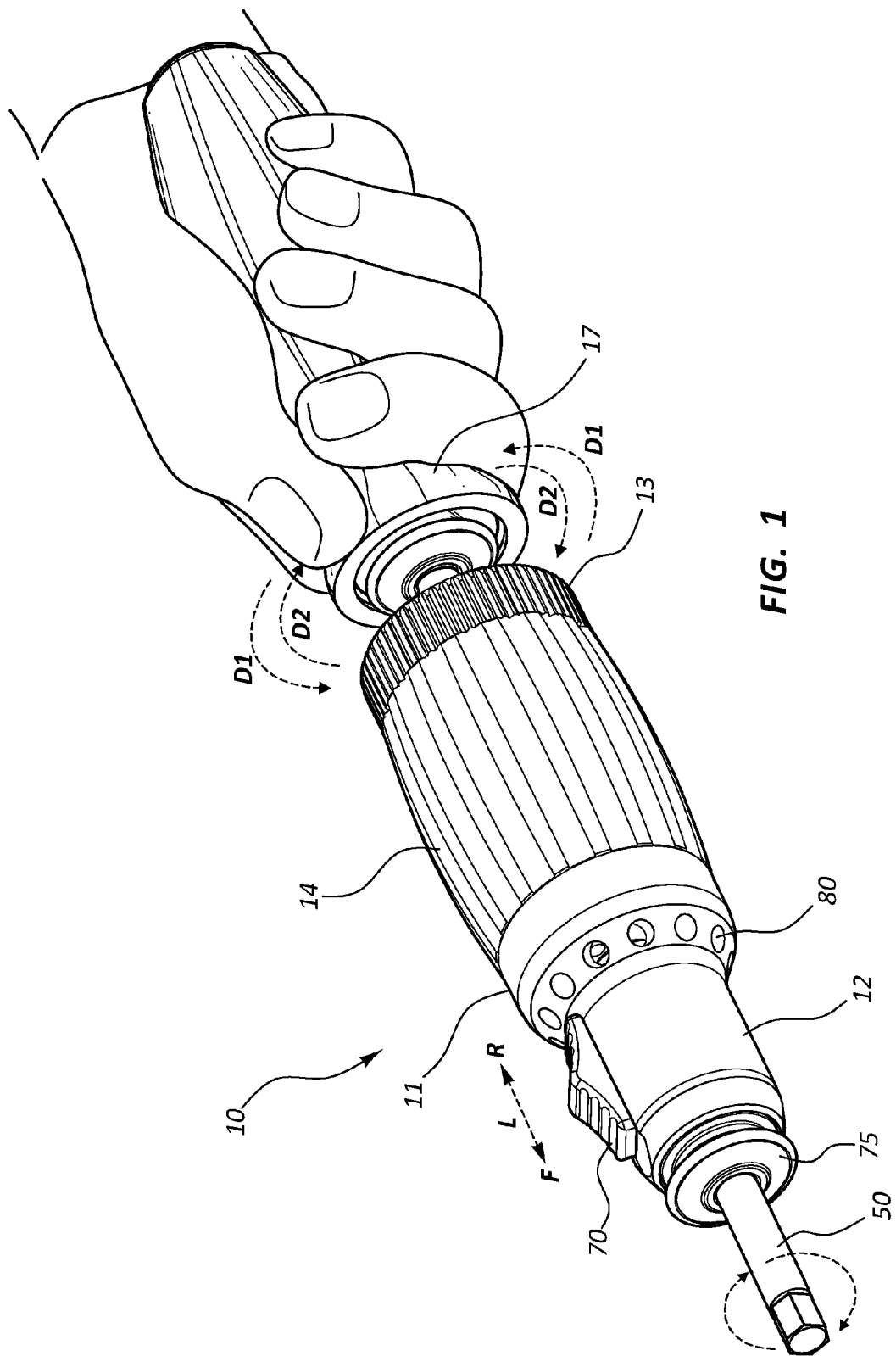
FIG. 1 illustrates an exemplary embodiment of a continuous ratchet medical instrument ("CRMI") adapter engaged and used with an output shaft and axial handle and directional arrows showing rotational direction of bi-directional input forces resulting in an output force in a single direction.

As used herein, the term "continuous" means capable of constant rotation in one direction without interruption or reversal.

As used herein, the term "cylindrical housing" means a cylindrically shaped barrel having an inner and outer surface, which houses mechanical components capable of translating bi-directional rotation inputs into a single directional output.

As used herein, the term "drive path" means the sequence of engagement of internal elements that transfers the input force into the output force.

As used herein, the term "front" means a location more proximal to the user.

As used herein, the term "non-rotating rear outer cap" means a stationary structure surrounding components capable of clockwise or counter-clockwise rotation.

As used herein, the term "one-quarter inch square input shaft" means a shaft having a square inner area with sides one-quarter square inch in length.

As used herein, the term "output shaft" means a shaft that can be received by an adapter capable of rotating an attached medical device in a pre-selected direction.

As used herein, the term "rear" means a location more distal to the user.

As used herein, the term "s-shaped aperture" means an s-shaped opening on an assembly, enabling components housed within the assembly to engage with components outside the assembly.

SUMMARY OF THE INVENTION

The present invention is a medical instrument adapter apparatus. This apparatus includes a rotating outer collar having an internal square adapter, at least one non-rotating rear outer cap, a cylindrical housing secured by a rear end cap and a bi-directional motion converting mechanism. The bi-directional motion converting mechanism includes a front drive gear shaft with front drive gear shaft teeth, a front pawl housing, a rear drive gear shaft with rear drive gear shaft teeth, a rear pawl housing, a triple-square drive gear, two differential drive gear shafts, each including differential drive gears, and a one-quarter inch square input shaft.

DETAILED DESCRIPTION OF INVENTION

For the purpose of promoting an understanding of the present invention, references are made in the text to exemplary embodiments of a continuous ratchet medical instrument adapter, only some of which are described herein. It should be understood that no limitations on the scope of the invention are intended by describing these exemplary embodiments. One of ordinary skill in the art will readily appreciate that alternate but functionally equivalent continuous drive ratchet mechanisms may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead emphasis has been placed upon illustrating the principles of the invention. In addition, in the embodiments depicted herein, like the reference numerals in the various drawings, refer to identical or near identical structural elements.

Moreover, the terms "about," "substantially" or "approximately" as used herein may be applied to modify any quantitative representation that could permissibly vary without resulting in a change in the basic function to which it is related.

FIG. 1 illustrates an exemplary embodiment of a continuous ratchet medical instrument ("CRMI") adapter in use with an output shaft 50 and axial handle 17, with directional arrows D1 and D2 showing the rotational direction of bi-directional input forces resulting in an output force in a single direction.

The embodiment shown in FIG. 1 shows an output shaft 50 inserted into collar 75 and the three position selector switch 70. Also illustrated in FIG. 1 are multiple flushing holes 80 traversing the outer circumference of the non-rotating rear outer cap 12 for cleaning and sterilization purposes. Also shown in FIG. 1 is an ergonomic, medically approved silicone sleeve 14 molded around the outer circumference of the cylindrical housing 11 for positive user grip in the operating room, and the grooved front end cap 13.

The CRMI adapter 10 is not a complete driver but an adapter used in conjunction with a medical ratcheting driver, non-ratcheting driver, medical torque wrench or other medical driving device. The CRMI adapter 10 is specifically designed for medical use, having no plastic parts, thus allowing sterilization in an autoclave.

The CRMI adapter 10 makes a clicking sound to help the doctor monitor rotation of the device.

FIG. 1 illustrates an embodiment of the CRMI adapter 10 capable of one handed and two-handed operation. For one-handed operation, the user grasps the axial handle 17 attached to the outer surface of the one-quarter inch square input shaft 16. For two handed operation, the user places one hand on the silicone sleeve 14, and places the other hand on the axial handle 17 attached to the outer surface of the one-quarter inch square input shaft 16.

Figure 2:
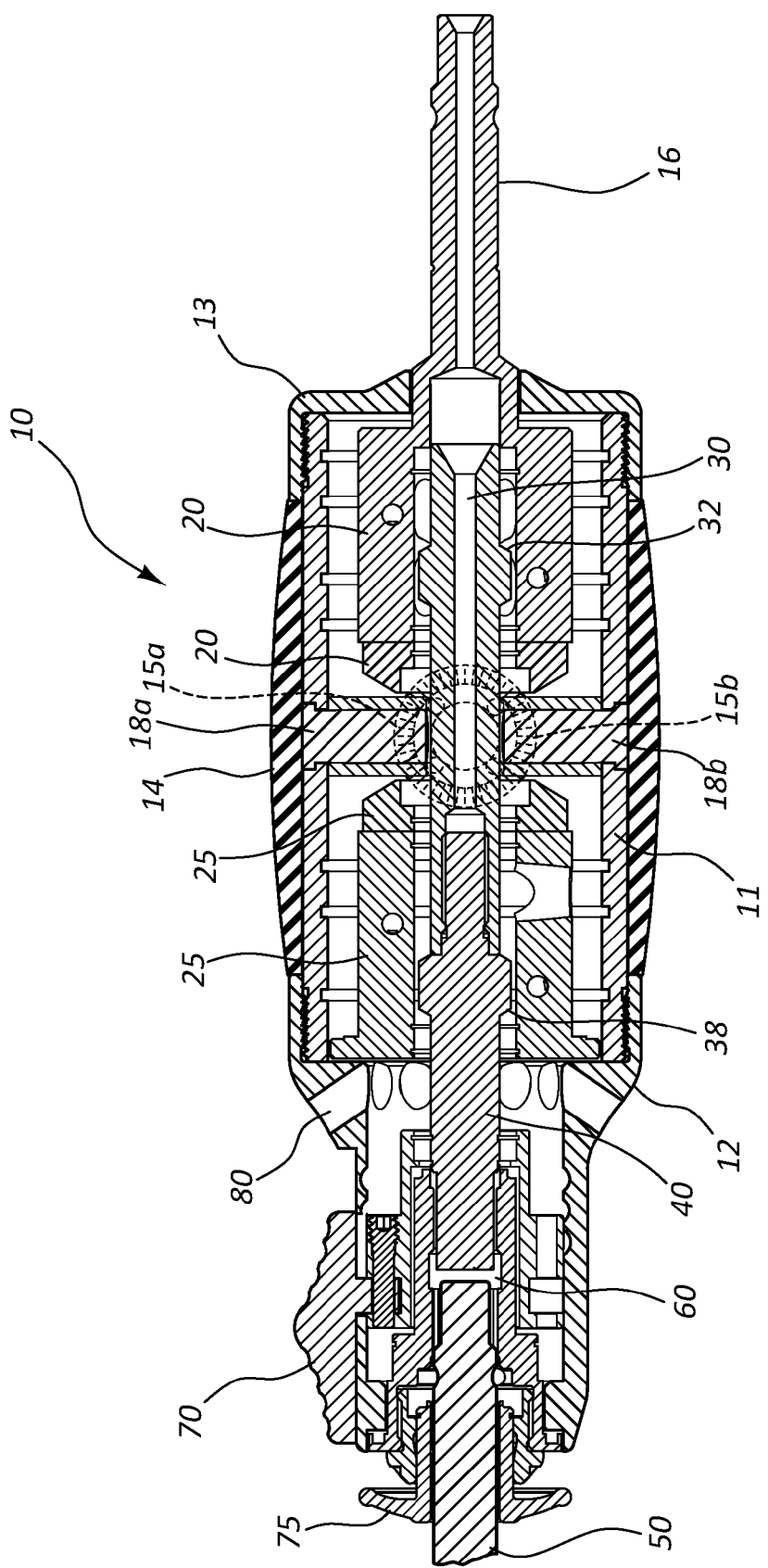
FIG. 2 is a cross sectional isometric view of an exemplary embodiment of a CRMI adapter.

FIG. 2 is a cross section view of an exemplary embodiment of a CRMI adapter 10. FIG. 2 shows a one-quarter inch square input shaft 16 perpendicular to the grooved front end cap 13, the front pawl housing 20 with integrally formed front drive gear shaft 30 having front drive gear shaft teeth 32. The front drive gear shaft 30 is operatively connected to the rear drive gear shaft 40 through the first differential gear shaft 18a having the first differential drive gear 15a and the second differential drive gear shaft 18b with differential gear 15b. FIG. 2 also illustrates the rear pawl housing 25 with integrally formed rear drive gear shaft 40 having rear drive gear teeth 38.

FIG. 2 also shows the location of multiple flushing holes 80 traversing the outer circumference of the non-rotating rear outer cap 12 with a three position selector switch 70, the triple square drive gear 60 at the junction of the rear drive gear shaft 40 and output shaft 50, and the internal one-quarter inch square adapter 68 with circular collar 75 situated about the outer circumference of output shaft 50.

Figure 3A:
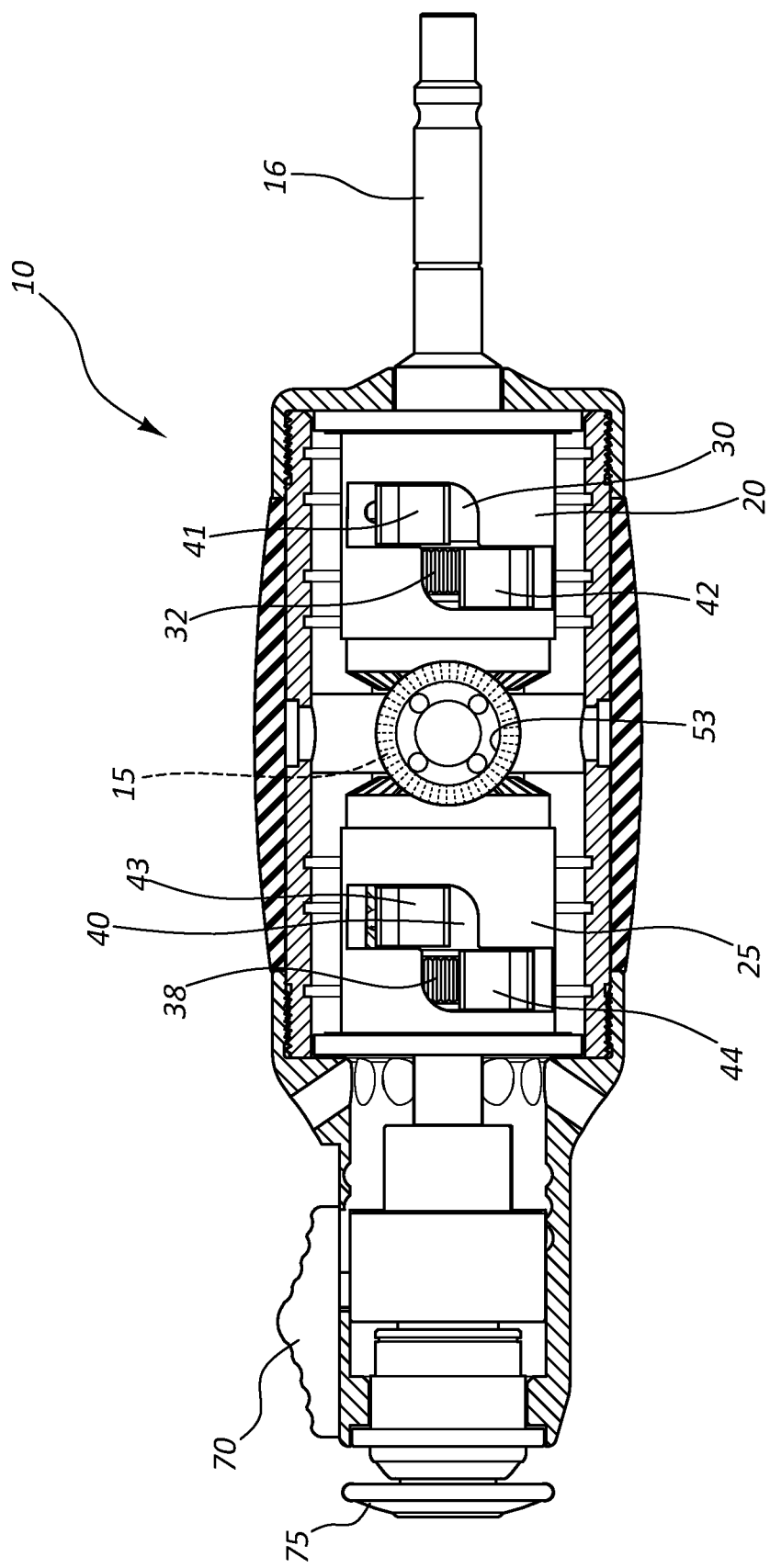
FIGS. 3a through 3c illustrate a single embodiment of the CRMI adapter with the selector switch in three alternate positions: forward, reverse, and locked.
Figure 3B:
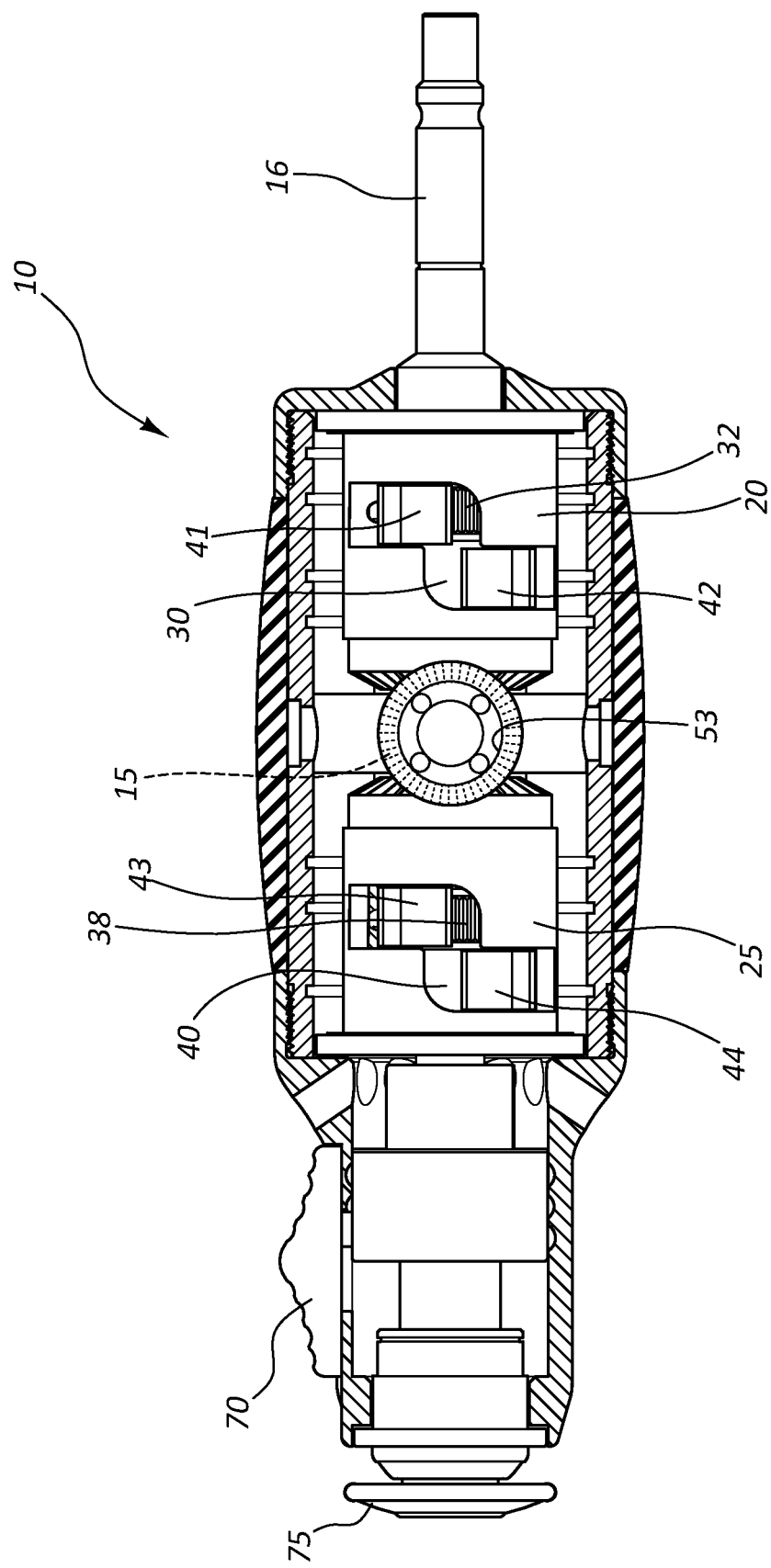
Figure 3C:
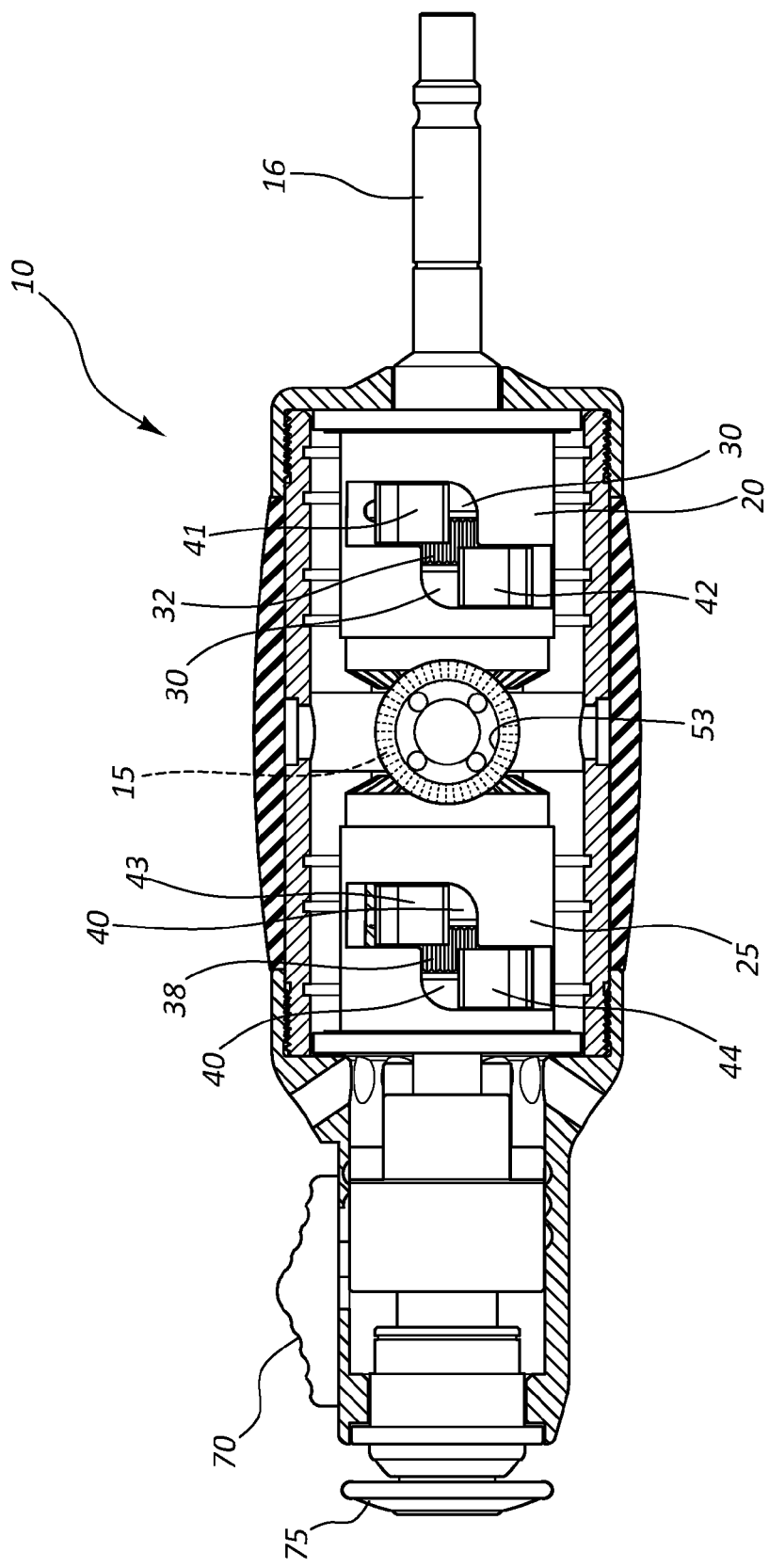

FIGS. 3a through 3c illustrate a single embodiment of the CRMI adapter 10 with the three position selector switch 70 in three alternate positions: forward, reverse, and locked.

As illustrated in FIGS. 3a, 3b, and 3c, a user toggles the three position selector switch 70 to select the direction of output rotation. The three positions are indicated relative to their orientation to the collar 75: F (forward towards the collar 75) for clockwise rotation, R (reverse) for counter-clockwise, and L (locked central position).

FIGS. 3a-3c illustrate the one-quarter inch square input shaft 16. They also illustrate the integrally formed front drive gear shaft 30 with front drive gear shaft teeth 32 visible in the figures through the s-shaped aperture 21 of the front drive pawl housing 20. The first front pawl 41 and second front pawl 42 are situated within the front pawl housing 20. FIGS. 3a-3c also show the first differential thrust bearings 53 and differential drive gears 15. The first rear pawl 43 and second rear pawl 44 are situated within the rear pawl housing 25, which has an s-shaped aperture 21. The integrally formed rear drive gear shaft 40 with rear drive gear shaft teeth 38 is visible through the rear pawl housing 25.

In the embodiment shown in FIG. 3b, the three position selector switch 70 is in the forward position (pushed towards the collar 75). In the forward position, two modes of operation are possible: one-handed operation and two-handed operation.

As shown in the embodiment illustrated in FIG. 3a, during operation with the three position selector switch 70 in the forward position, rotation of the one-quarter inch square input shaft 16 in a clockwise direction drives the front pawl housing 20 to rotate in a clockwise direction. The first front pawl 41 is not engaged with the front drive gear shaft teeth 32, while the second front pawl 42 is engaged with the front gear drive shaft teeth 32 situated in the front drive gear shaft 30, and drives the first differential gear 15a and the second differential gear 15b. The first and second differential gears 15a and 15b drive the rear pawl housing 25 to rotate in a counter-clockwise direction. The first rear pawl 43 is not engaged on the rear drive gear shaft teeth 38 situated within the rear drive gear shaft 40, and the second rear pawl 44 is ratcheting, i.e., engaged with the rear drive gear shaft teeth 32, but not driving the rear drive gear shaft 40. The rear gear drive shaft 40 is attached to and drives the triple-square drive gear 60, which drives the output shaft 50 in a clockwise direction.

During operation with the three position selector switch 70 in the forward position as shown in the embodiment in FIG. 3a, rotation of the one-quarter inch square input shaft 16 in a counter-clockwise direction drives the front pawl housing 20 to rotate in a counter-clockwise direction. The second front pawl 42 is engaged with the front gear drive shaft teeth 32, but not driving the front drive gear shaft 30, while the first front pawl 41 is not engaged with the front drive gear shaft teeth 32. The first and second differential gears 15a and 15b, respectively, drive the rear pawl housing 25 to rotate in a clockwise direction. The first rear pawl 43 is not engaged on the rear drive gear shaft teeth 38, while the second rear pawl 44 is engaged with the rear drive gear shaft teeth 38 and drives the rear drive gear shaft 40. The rear gear drive shaft 40 is attached to and drives the triple-square drive gear 60, which drives the output shaft 50 in a clockwise direction.

In the embodiment shown in FIG. 3a, one handed operation translates a clockwise rotation of the one-quarter inch square input shaft 16 into a clockwise rotation of the output shaft 50, and two handed operation translates a counter-clockwise rotation of the one-quarter inch square input shaft 16 into clockwise rotation of the output shaft 50.

In the embodiment shown in FIG. 3b, the three position selector switch 70 is in the reverse position (pushed away from the collar 75). In the reverse position, two modes of operation are possible: one-handed operation and two-handed operation.

As shown in the embodiment illustrated in FIG. 3b, during operation with the three position selector switch 70 in the reverse position, rotation of the one-quarter inch square input shaft 16 in a clockwise direction drives the front pawl housing 20 to rotate in a clockwise direction. The second front pawl 42 is not engaged with the front gear drive shaft teeth 32, while the first front pawl 41 is ratcheting, i.e., engaged with the front drive gear shaft teeth 32, but not driving the front drive gear shaft 30. The differential gears 15a and 15b drive the rear pawl housing 25 to rotate in a counter-clockwise direction. The second rear pawl 44 is not engaged on the rear drive gear shaft teeth 38, while the first rear pawl 43 is engaged with the rear drive gear shaft teeth 38 and drives the rear drive gear shaft 40. The rear gear drive shaft 40 is attached to and drives the triple-square drive gear 60, which drives the output shaft 50 in a counter-clockwise direction.

As illustrated by the embodiment shown in FIG. 3b, during operation with the three position selector switch 70 in the reverse position, rotation of the one-quarter inch square input shaft 16 in a counter-clockwise direction drives the front pawl housing 20 to rotate in a counter-clockwise direction. The first front pawl 41 is engaged with the front gear drive shaft teeth 32 and drives the front drive gear shaft 40, while the first front pawl 41 is not engaged with the front drive gear shaft teeth 32. The differential gears 15a and 15b drive the rear pawl housing 25 to rotate in a clockwise direction. The second rear pawl 44 is not engaged with the rear drive gear shaft teeth 38, while the first rear pawl 43 is ratcheting, i.e., engaged on the rear drive gear shaft teeth 38, but not driving the rear drive gear shaft 40. The rear gear drive shaft 40 is attached to and drives the triple-square drive gear 60, which drives the output shaft 50 in a counter-clockwise direction.

In the embodiment shown in FIG. 3b, one handed operation translates a counter-clockwise rotation of the one-quarter inch square input shaft 16 into a counter-clockwise rotation of the output shaft 50, and two handed operation translates a clockwise rotation of the one-quarter inch square input shaft 16 into a counter-clockwise rotation of the output shaft 50.

In the embodiment shown in FIG. 3c, the three position selector switch 70 is in a central position relative to the collar 75. In the locked position, only the one-handed mode of operation is possible, enabling the entire instrument to perform the same function as an extension to a driver.

As illustrated in the embodiment shown in FIG. 3c, during operation in the locked position, a clockwise rotation of the one-quarter inch square input shaft 16 does not result in rotation of the front pawl housing 20. The first front pawl 41 is touching the front drive shaft gear teeth 32 and could ratchet, while the second front pawl 42 is engaged with the front drive gear shaft teeth 32 and could drive the front drive gear shaft 30. The differential gears 15a and 15b could drive the rear pawl housing 25. The first rear pawl 43 is touching the rear drive gear shaft teeth 38 and could ratchet, while the second rear pawl 44 is engaged with the rear drive gear shaft teeth 38 and could drive the rear drive gear shaft 40. The results in no rotational movement of the front pawl housing 20 or rear pawl housing 25 upon clockwise rotation of the one-quarter inch square input shaft 16 because the front pawl housing 20 and rear pawl housing 25 are locked in place by the second front pawl 42 and the second rear pawl 44. Clockwise rotation of the one-quarter inch square input shaft 16 drives the triple square drive gear 60 to rotate in a clockwise direction, resulting in clockwise rotation of the output shaft 50.

As illustrated in the embodiment shown in FIG. 3c, during operation in the locked position, a counter-clockwise rotation of the one-quarter inch square input shaft 16 does not result in rotation of front pawl housing 20. The second front pawl 42 is touching the front drive shaft gear teeth 32 and could ratchet, while the first front pawl 41 is engaged with the front drive gear shaft teeth 32 and could drive the front drive gear shaft 30. The differential gears 15a and 15b could drive the rear pawl housing 25. The second rear pawl 44 is touching the rear drive gear shaft teeth 38 and could ratchet, while the first rear pawl 43 is engaged with the rear drive gear shaft teeth 38 and could drive the rear drive gear shaft 40. The result is no rotational movement of the front pawl housing 20 or rear pawl housing 25 upon counter clockwise rotation of the one-quarter inch square input shaft 16 because the front pawl housing 20 and rear pawl housing 25 are locked in place by the first front pawl 41 and the first rear pawl 43, respectively. A counter clockwise rotation of the one-quarter inch square input shaft 16 drives the triple square drive gear 60 to rotate in a counter-clockwise direction, resulting in a counter-clockwise rotation of the output shaft 50.

In the embodiment shown in FIG. 3c, clockwise rotation of the one-quarter inch square input shaft 16 results in clockwise rotation of the output shaft 50 at the same speed as the one-quarter inch square input shaft 16. In the embodiment shown in FIG. 3c, counter-clockwise rotation of the one-quarter inch square input shaft 16 results in counter-clockwise rotation of the output shaft 50 at the same speed as the one-quarter inch square input shaft 16.

Figure 4:
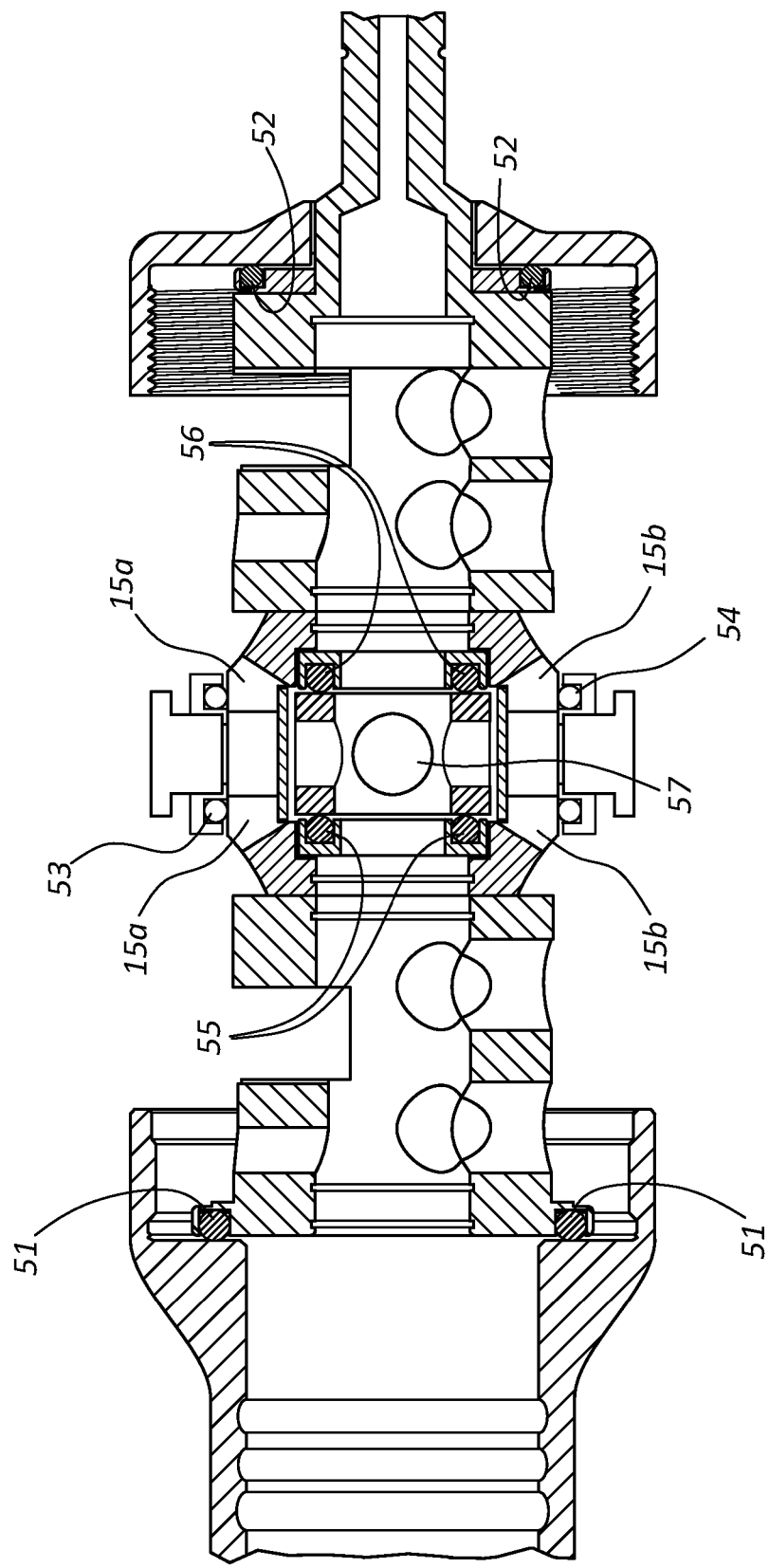
FIG. 4 is an isometric cross sectional view of an exemplary embodiment of a CRMI adapter showing the central housing and locations of the thrust bearings and front and rear gear drive shafts.

FIG. 4 is an exploded cross section view of an exemplary embodiment of a CRMI adapter 10 showing the center housing 57 and locations of the rear drive thrust bearings 51, front drive thrust bearings 52, the first differential drive thrust bearings 53 adjacent to the differential drive gear 15a and the second differential drive thrust bearings 54 adjacent to the differential drive gear 15b, and the center housing 57 with first center differential drive thrust bearings 55 and second center differential drive thrust bearings 56.

Figure 5:
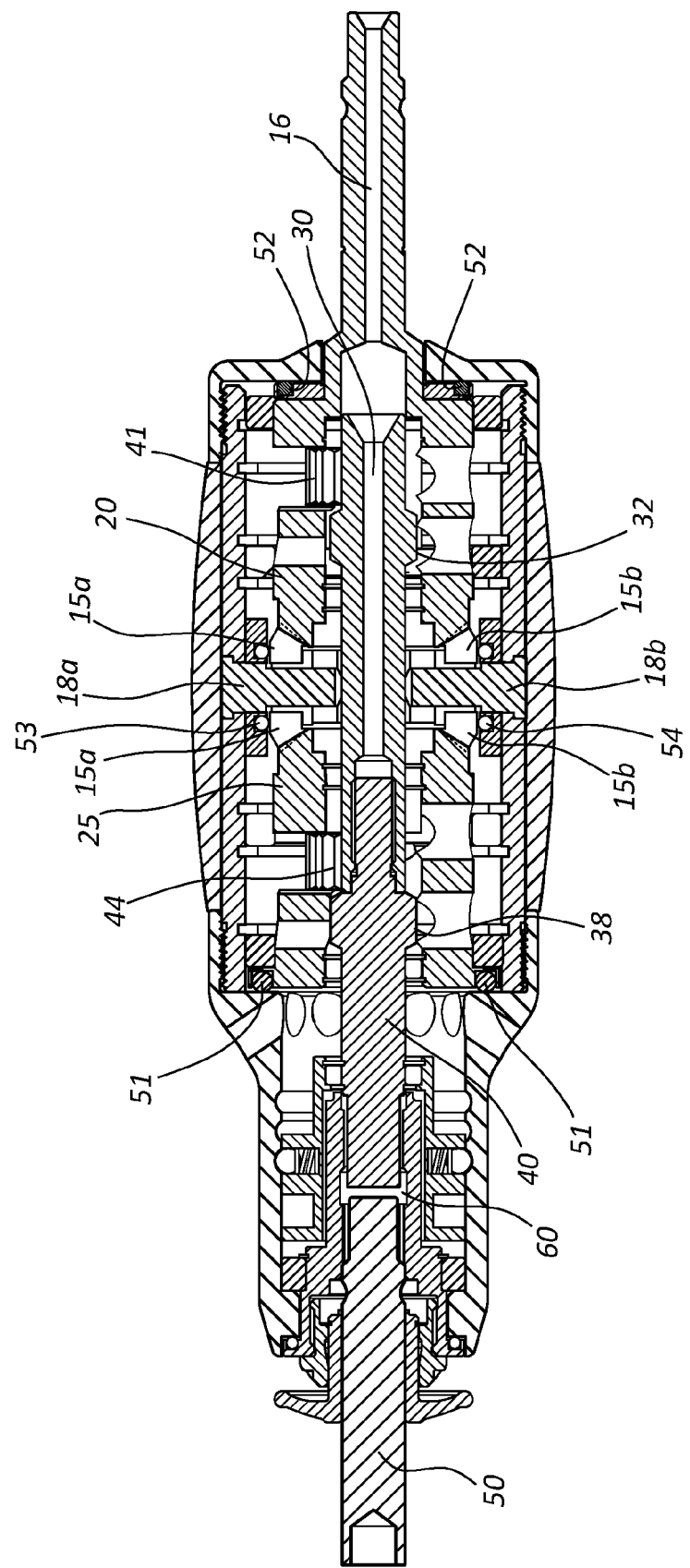
FIG. 5 is an isometric cross sectional view of an exemplary embodiment of a CRMI adapter that illustrates the use of thrust bearings.

FIG. 5 is an isometric cross section view of an exemplary embodiment of a CRMI adapter 10 which illustrates the use of thrust bearings to facilitate reliability in the operating room and to prevent galling between the metal surfaces FIG. 5 shows the front drive thrust bearings 52 in a ring configuration about the outer circumference of the one-quarter inch square input shaft 16. As thrust bearings 52 are situated between the outer surface of the one-quarter inch square input shaft 16 and inner surface of the front end cap 13 (not labeled), they prevent direct contact between the components. FIG. 5 also illustrates the integrally formed front drive shaft 30 running through the front pawl housing 20. In the embodiment shown in FIG. 5, the front drive gear shaft teeth 32 are engaged with second front pawl 42 (not shown) and the first front pawl 41 is not engaged.

FIG. 5 further shows the first differential drive thrust bearing 53 in a ring configuration about the outer circumference of the differential drive gear shaft 18a to facilitate smooth rotation of the first differential drive gear 15a about the differential drive gear shaft 18a. FIG. 5 also shows the second differential drive thrust bearing 54 in a ring configuration about the outer circumference of the differential drive gear shaft 18b to facilitate smooth rotation of the second differential drive gear 15b about the differential drive gear shaft 18b.

FIG. 5 further shows the rear drive thrust bearings 51 in a ring configuration about the rear pawl housing 25 with integrally formed rear drive gear shaft 40. In the embodiment shown in FIG. 5, the rear drive gear shaft teeth 38 are engaged with the first rear pawl 43 (not shown) and the second rear pawl 44 is not engaged. FIG. 5 shows the triple square drive gear 60 situated at the junction of the rear drive gear shaft 40 and output shaft 50.

As illustrated in FIG. 5, the CRMI adapter 10 secures specialized medical tools internally by means of an internal bit locking mechanism (BMI patent), and has no external screwdriver bit holder.

Figure 6B:
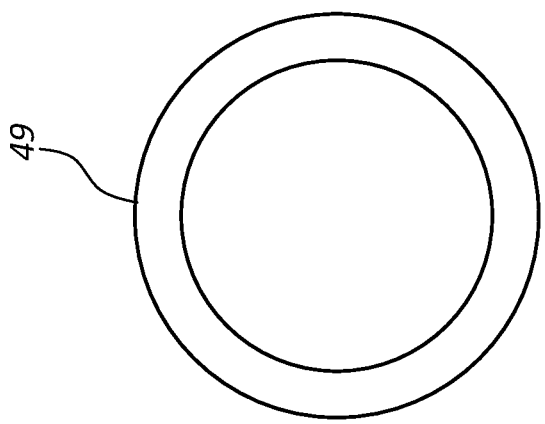
FIG. 6b shows a top view of a prior art bearing.
Figure 6A:
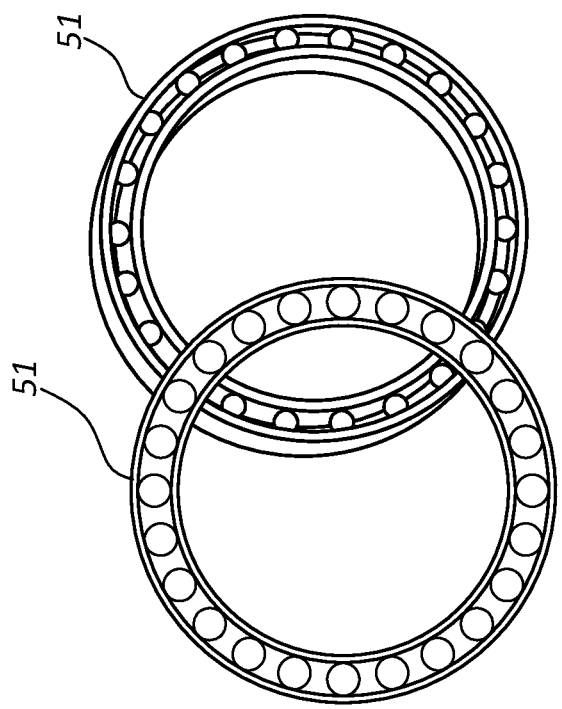
FIG. 6a shows a top and a perspective view of two embodiments of the rear drive thrust bearings.

FIG. 6a shows a top and a perspective view of two embodiments of the rear drive thrust bearings 51. The use of numerous thrust ball bearings in a ring configuration instead of a standard sleeve design (seen in FIG. 6b) facilitates use of the CRMI adapter 10 in a non-lubricated environment. Eliminating the use of lubricants also enables sterilization of the CRMI adapter 10 in an autoclave.

What is claimed is:

1. A medical instrument adapter apparatus comprised of:
   a rotating outer collar having an internal square adapter;
   at least one non-rotating rear outer cap;
   a cylindrical housing secured by a rear end cap;
   a bi-directional motion converting mechanism comprised of:
   a front drive gear shaft comprising front drive gear shaft teeth;
   a front pawl housing;
   a rear drive gear shaft comprising rear drive gear shaft teeth;
   a rear pawl housing;
   a triple-square drive gear;
   two differential drive gear shafts each comprising differential drive gears; and
   a one-quarter inch square input shaft.

2. The apparatus of claim 1 wherein said rotating outer collar is capable of clockwise or counter-clockwise rotation.

3. The apparatus of claim 1 wherein said non-rotating rear outer cap further comprises multiple holes traversing the circumference of said rear outer cap for flushing during cleaning and sterilization.

4. The apparatus of claim 1 wherein said non-rotating rear outer cap further comprises a selector switch assembly comprised of a three-position selector switch capable of front, reverse, and locked position.

5. The apparatus of claim 1 wherein said cylindrical housing comprises a silicone sleeve molded to the outer surface of said cylindrical housing for positive user grip during surgical procedures.

6. The apparatus of claim 1 wherein said internal square adapter is configured to automatically engage and release an output shaft for the purpose of attaching and releasing medical instruments.

7. The apparatus of claim 1 wherein said front pawl housing further comprises an s-shaped aperture.

8. The apparatus of claim 1 wherein said rear pawl housing further comprises an s-shaped aperture.

9. The apparatus of claim 1 wherein said front pawl housing further comprises a first front pawl and a second front pawl.

10. The apparatus of claim 9 wherein said front pawl housing further comprises an integrally formed front drive gear shaft, wherein said front drive gear shaft comprises a plurality of front drive gear shaft teeth capable of engaging said first front pawl or said second front pawl to drive said differential gears.

11. The apparatus of claim 10 wherein said front drive gear shaft comprises front drive thrust bearings situated at the junction of said front drive gear shaft and said front end cap for use in a non-lubricated environment.

12. The apparatus of claim 10 wherein said front drive gear shaft is operatively coupled to a rear drive gear shaft by means of said two differential gear shafts, wherein said differential gear shafts comprise differential gears.

13. The apparatus of claim 12 wherein said differential gear shafts are operatively connected by a center housing, wherein said center housing comprises four center differential drive thrust bearings situated in all four directions for use in a non-lubricated environment.

14. The apparatus of claim 1 wherein said rear pawl housing further comprises a first rear pawl and a second rear pawl.

15. The apparatus of claim 14 wherein said rear pawl housing further comprises an integrally formed rear drive gear shaft, wherein said rear drive gear shaft comprises rear drive gear shaft teeth capable of engaging said first rear pawl or said second rear pawl to drive said rear drive gear shaft.

16. The apparatus of claim 15 wherein said rear drive gear shaft is capable of driving said triple-square drive gear to rotate in a clockwise or counter-clockwise direction.

17. The apparatus of claim 15 wherein said rear drive gear shaft comprises rear drive thrust bearings situated at the junction of said rear drive gear shaft and said output shaft for use in a non-lubricated environment.

18. The apparatus of claim 1 wherein said triple-square drive gear is capable of driving said output shaft to rotate in a clockwise or counter-clockwise direction.

19. The apparatus of claim 1 wherein said one-quarter inch square input shaft is capable of mounting an axial handle and is capable of clockwise or counter-clockwise rotation.

20. The apparatus of claim 1, wherein said one-quarter inch square input shaft is capable of driving the said front pawl housing to rotate in a clockwise or counterclockwise direction.

* * * * *